US00PP08223P

United States Patent [19]

VandenBerg

[11] Patent Number: Plant 8,223

[45] Date of Patent: May 11, 1993

[54] CHRYSANTHEMUM PLANT NAMED DARK BRIOSO

[75] Inventor: Cornelis P. VandenBerg, Salinas, Calif.

[73] Assignee: Yoder Brothers, Inc., Barberton, Ohio

[21] Appl. No.: 701,088

[22] Filed: May 16, 1991

[51] Int. Cl.[5] ..... A01H 5/00

[52] U.S. Cl. ..... Plt./74.1

[58] Field of Search ..... Plt. 74.1, 82.4, 82.5

[56] References Cited

U.S. PATENT DOCUMENTS

Plt. 6,497 12/1988 VandenBerg ..... Plt. 74

4,616,099 10/1986 Sparkes ..... 800/1

OTHER PUBLICATIONS

Gosling, ed., 1979, "The Chrysanthemum Manual-6th Edition", The National Chrysanthemum Society, London, Essex Telegraph Press, Ltd., pp. 329-336.

Broertjes et al., 1978. "Application of Mutation Breeding Methods in the Improvement of Vegetatiaily Propagated Crops", Elsevier Sci. Pub. Co., New York, pp. 162-175.

Broertjes et al., 1980. "A Mutant of a Mutant of a Mutant of a . . . Irradiation of Progressive Radiation-Induced Mutants in a Mutation Breeding Programme with *Chrysanthemum Morifolium*", Euphytica 29:526-530.

Searle et al. 1968. "Chrysanthemums the Year Round", Blanford Press, London, pp. 27-29, 320-327.

Chan. 1966. "Chrysanthemum and Rose Mutations Induced by X-Rays", Am. Soc. Hort. Sci. Proc. pp. 613-620.

Broertjes. 1966. "Mutation Breeding of Chrysanthemums", Euphytica, 15:156-162.

Dowrick et al. 1966. "The Induction of Mutations in Chrysanthemums Using X-and Gamma Radiation. Euphytica", 15:204-210.

*Primary Examiner*—Howard J. Locker

*Attorney, Agent, or Firm*—Foley & Lardner

[57] ABSTRACT

A Chrysanthemum plant named Dark Brioso particularly characterized by its flat capitulum form; daisy capitulum type; red-purple ray floret color; diameter across face of capitulum of 108 to 114 mm when fully opened, when grown as a single stem spray cut mum; photoperiodic flowering response to short days to 52 to 68 days; and plant height, with 14 long days after planting rooted cuttings prior to start of short days and with no growth regulator applications, ranges from 109 to 117 cm when grown as a single stem cut mum.

1 Drawing Sheet

The present invention comprises a new and distinct cultivar of Chrysanthemum, botanically known as *Dendranthema grandiflora*, and referred to by the cultivar name Dark Brioso.

Dark Brioso, identified as 2834 (83-678A09), is a product of a mutation induction program. The new cultivar was discovered and selected by Cornelis P. VandenBerg in March 1987 in a controlled environment in Salinas, Calif., as one flowering plant within a flowering block established as rooted cuttings from stock plants which had been epxosed as unrooted cuttings to an x-ray source of 2000 rads in Fort Myers, Fla., in October 1986. The irradiated parent cultivar was the cultivar identified as Brioso, disclosed in U.S. Plant Pat. No. 6,497.

The irradiation program resulting in Dark Brioso had as its primary objective the expansion of color ranges of the parent cultivar Brioso. The irradiation program comprised irradiating cuttings of the parent cultivar at irradiation levels of 1500, 1750 and 2000 rads. A total of 593 cuttings harvested from a total of 225 irradiated plants were planted on Feb. 9, Feb. 2 and Jan. 12, 1987, respectively. Of these, 13 initial selections were made, which selections were then revegetated and reflowered. Four consecutive flowerings resulted in discarding 9 of the original 13 selections on Jan. 12, 1988. Three selections were retained as possible introductions, and one selection was retained for possible re-irradiation to obtain a yellow mutation of Brioso, which color was not present in the original selections. The three retained selections will be commercially introduced as Dark Brioso, Light Brioso and Bronze Brioso. The retained selection for possible re-irradiation yielded a spontaneous yellow mutation, which will be commercially introduced as Yellow Brioso. The cultivars Light Brioso, Bronze Brioso and Yellow Brioso are disclosed in pending plant patent applications of applicant.

The first act of asexual reproduction of Dark Brioso was accomplished when vegetative cuttings were taken from the initial selection in May 1987 in a controlled environment in Salinas, Calif., by technicians working under supervision of Cornelis P. Vandenburg.

Horticultural examination of controlled flowerings of successive plantings has shown that the unique combination of characteristics as herein disclosed for Dark Brioso are firmly fixed and are retained through successive genrations of asexual reproduction.

Dark Brioso has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Dark Brioso, which, in combination, distinguish this Chrysanthemum as a new and distinct cultivar:

1. Flat capitulum form.
2. Daisy capitulum type.

3. Red-purple ray floret color.

4. Diameter across face of capitulum of 108 to 114 mm when fully opened, when grown as a single stem cut mum.

5. Photoperiodic flowering response to short days of 52 to 68 days.

6. Plant height, with 14 long days after planting rooted cuttings prior to start of short days and with no growth regulator applications, ranges from 109 to 117 cm when grown as a single stem cut mum.

The accompanying photographic drawing is a view of a single stem of Dark Brioso, with the colors being as nearly true as possible with illustrations of this type.

Of the commercial cultivars known to the inventor, the most similar in comparison to Dark Brioso is the parent cultivar Brioso. All traits of Dark Brioso are similar to those of Brioso, except for the ray floret color. The ray floret color of Dark Brioso is a significantly darker and more reddish purple than the ray floret color of Brioso. In two evaluations, it was noted that flower diameter of Dark Brioso was slightly smaller than the diameter of the parent Brioso. However, no exact measurements were taken. The parent cultivar Brioso was never commercially introduced in Colombia, South America, because of low production of flowers per stem, and low night temperature tolerance of the Brioso sports was not evaluated in Colombia.

In the following description color references are made to The Royal Horticultural Society Colour Chart. The color values were determined on plant material grown as a single stem spray cut mum in Salinas, Calif. on Jun. 20, 1990.

Classification:

*Botanical.*—*Dendranthema grandiflora* cv Dark Brioso.

*Commercial.*—Flat daisy spray cut mum.

INFLORESCENCE

A. Capitulum:

*Form.* Flat.

*Type.*—Daisy.

*Diameter across face*—. 108 to 114 mm when fully opened.

B. Corolla of ray florets:

*Color (general tonality from a distance of three meters).*—Red-purple.

*Color (upper surface).*—70B, slightly grainy.

*Color (under surface).*—77D, strongly overlaid with 70B.

*Shape.*—Oblong

C. Corolla of disc florets:

*Color (mature).*—14A

*Color (immature).*—144B, with tingeing in the center closest to R.H.S. 166A providing a dark appearing central eye which essentially disappears when the disc florets are fully mature.

D. Reproductive organs:

*Androecium.*—Present on disc florets only; scant pollen.

*Gynoecium.*—Present on both ray and disc florets.

PLANT

A. General appearance:

*Height.*—109 to 117 cm when grown as a single stem cut mum with 14 long days after planting rooted cuttings prior to start of short days and no growth regulator applications.

B. Foliage:

*Color (upper surface).*—174A.

*Color (under surface).*—147B.

*Shape.*—Lobed and slightly serrated.

I claim:

1. A new and distinct Chrysanthemum plant named Dark Brioso, as described and illustrated.

* * * * *

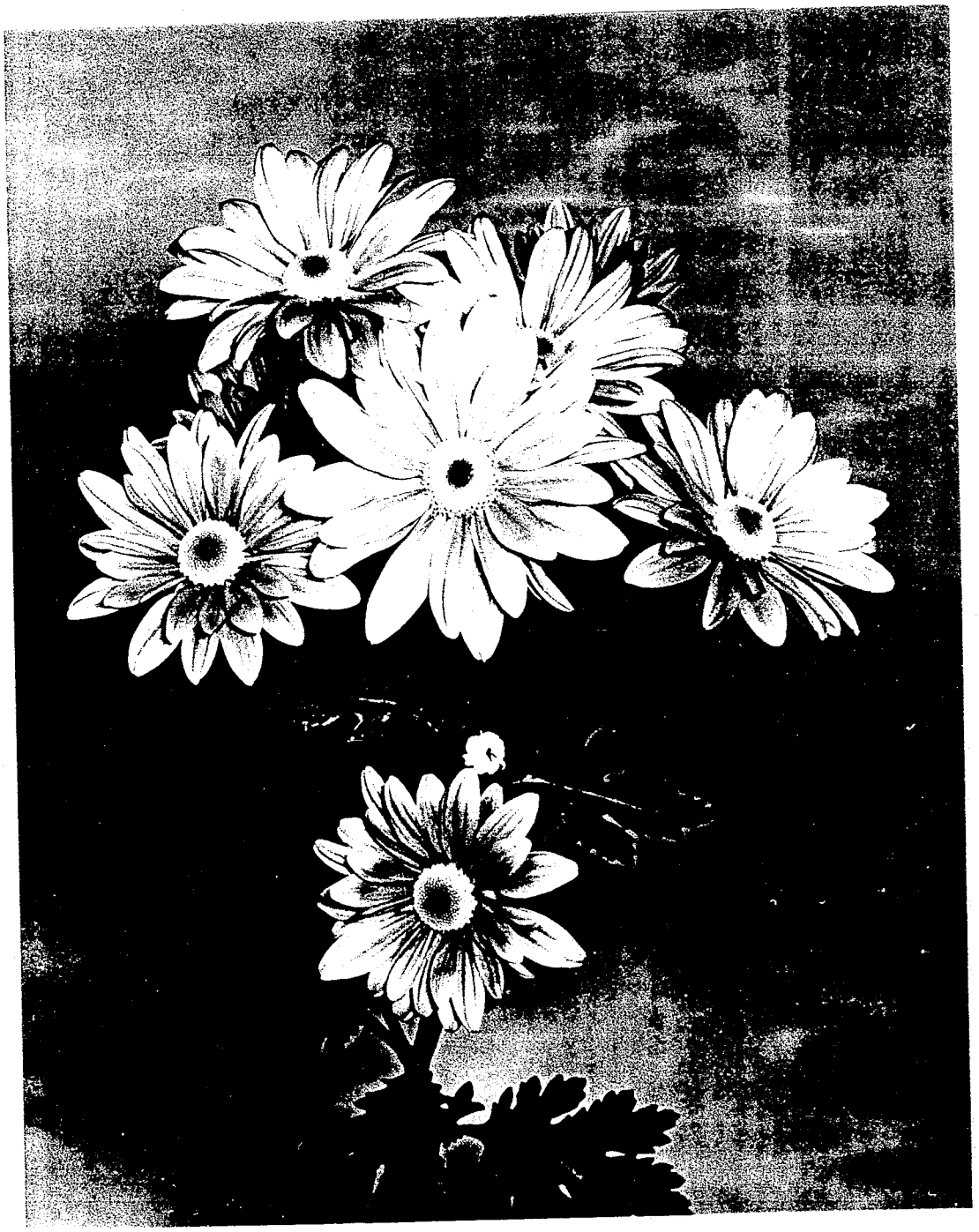

UNITED STATES PATENT AND TRADEMARK OFFICE

CERTIFICATE OF CORRECTION

PATENT NO. : PP 8,223

DATED : May 11, 1993

INVENTOR(S) : Cornelis P. VandenBerg

It is certified that error appears in the above-indentified patent and that said Letters Patent is hereby corrected as shown below:

Column 2, line 11, "Vandenburg" should read --VandenBerg--.

Column 4, line 33, "174A" should read --147A--.

Signed and Sealed this

Twenty-first Day of June, 1994

*Attest:*

Bruce Lehman

BRUCE LEHMAN

*Attesting Officer*

*Commissioner of Patents and Trademarks*